(12) United States Patent
Chao (10) Patent No.: US 10,835,915 B2
(45) Date of Patent: Nov. 17, 2020

(54) ESSENCE ATOMIZER HAVING INTEGRALLY FORMED UNIVERSAL CONNECTOR

(71) Applicants: Hsuan-Yu Chao, Taipei (TW); Mei-Mei Tsai, Taipei (TW)

(72) Inventor: Hsuan-Yu Chao, Taipei (TW)

(73) Assignees: Hsuan-Yu Chao, Taipei (TW); Mei-Mei Tsai, Taipei (TW)

( * ) Notice: Subject to any disclaimer, the term of this patent is extended or adjusted under 35 U.S.C. 154(b) by 157 days.

(21) Appl. No.: 16/027,189

(22) Filed: Jul. 3, 2018

(65) Prior Publication Data

US 2020/0009599 A1 Jan. 9, 2020

(51) Int. Cl.
*B05B 17/06* (2006.01)

(52) U.S. Cl.
CPC .................. *B05B 17/063* (2013.01)

(58) Field of Classification Search
CPC ... B05B 17/06; B05B 17/0607; B05B 17/063; A61M 15/001; A61M 15/0085
USPC ...................... 239/102.2, 376–379
See application file for complete search history.

(56) References Cited

U.S. PATENT DOCUMENTS

2019/0232319 A1 * 8/2019 Ou ...................... B05B 17/0607
2019/0283067 A1 * 9/2019 Nanda ...................... A61L 9/22

FOREIGN PATENT DOCUMENTS

WO    WO-2018040995 A1 * 3/2018 ............ A61M 11/00

* cited by examiner

*Primary Examiner* — Jason J Boeckmann
(74) *Attorney, Agent, or Firm* — Chun-Ming Shih; HDLS IPR Services (57) ABSTRACT

Disclosed is an essence atomizer having an integrally formed universal connector, comprising: an atomizer universal connector integrally formed into a pipe piece, and an outer shell. Wherein, the pipe port of the first end portion is greater than the pipe port of the second end portion. On the pipe port of the first end portion is disposed inward in sequence a front connection port, the inner threads, and a bottom groove for placing a rubber ring. While on the pipe port of the second end portion is disposed an expansion ring connected to an atomizer plate, an oil prevention pad, and a nozzle cover. The essence atomizer is compact in size and simple in structure Since the essence atomizer is integrally formed into a piece, so it requires less components, and the production process can be reduced.

2 Claims, 8 Drawing Sheets

ESSENCE ATOMIZER HAVING INTEGRALLY FORMED UNIVERSAL CONNECTOR

BACKGROUND OF THE INVENTION

Field of the Invention

The present invention relates to an ultrasonic atomizing technology, and in particular to an essence atomizer having an integrally formed universal connector.

The Prior Arts

In recent years, due to the rapid progress and development of the medical science and cosmetics industry, people are able to pay more attention to their medical health cares, and to keep a pleasing appearance. In this respect, ultrasonic aroma diffuser, beauty/health care device, water and essence mist humidifier, essence diffuser, etc. are utilized extensively in beauty shops and ordinary households, and that is realized by using the ultrasonic atomizing technology. As such, through the high frequency vibrations of the atomizing plate, the essence liquid in the container is atomized into minute particles of mist, for diffusing it into the surroundings.

The early design of the ordinary ultrasonic essence diffuser is rather insufficient. In application, the essence liquid in an essence container available on the market has to be dispensed into a specific container, then the specific container is installed on the essence diffuser to perform the essence atomizing function, thus causing quite inconvenience for a user. To overcome this deficiency, in U.S. Pat. No. 9,623,137B2, the applicant of the present invention proposed an Essential Oil Diffuser, for which the essence container presently available on the market can be screwed directly into the connector shell of the diffuser main body for use, without the need to purchase other container article or to perform dispensing actions. Though, that Essential Oil Diffuser is easy to use, and can be screwed an essence container therein at any time to perform essence therapy, yet it requires to use quite a lot of components and therefore its cost is high.

In particular, in that patent, the part of the essential oil diffuser connector outer pipe used to connect to the essence container is not integrally formed into a body. In contrast, it is formed by docking and packaging a left half portion and a right half portion together. Thus, in manufacturing, it requires secondary processing. Further, in application, in face of volatility and dissolvability of the essence liquid, the water tight seal for the part connecting to the essence container is liable to be damaged after long time usage, thus leading to leakage and waste of essence liquid. Therefore, this major shortcoming of the present technology has to be overcome urgently and effectively.

SUMMARY OF THE INVENTION

In view of the problems and drawbacks of the prior art, the present invention provides an essence atomizer having an integrally formed universal connector, comprising: an atomizer universal connector formed integrally into a pipe piece, having a first end portion and a second end portion opposite to the first end portion, the first end portion is of a cylindrical shape, while the second end portion is of a tapering protrusion shape, an inside bend portion is disposed between the first end portion and a second end portion, a pipe port of the second end portion forms an angle with a pipe port of the first end portion, the pipe port of the first end portion is greater than the pipe port of the second end portion, on the pipe port of the first end portion is disposed inward in sequence a front connection port, inner threads, and a bottom groove for placing a rubber ring, to form a universal connector connected to an opposite essence container, on the pipe port of the second end portion is disposed an expansion ring connected to an atomizer plate, an oil prevention pad, a nozzle cover formed into a protrusion plate having a hole; and an outer shell, used to wrap around and cover the atomizer universal connector, and an electric circuit board connected thereto. A placement port is disposed at the first end portion of the atomizer universal connector opposite to the outer shell. A sprout is disposed at the nozzle cover opposite to the second end portion A DC power jack is disposed on the outer shell, for connecting to a DC power source, to supply power to the electric circuit board. And a control key on the outer shell is connected to the electric circuit board, the electric circuit board is connected to and controls the atomizer plate to work.

Compared with the Prior Art, the present invention has the advantages in that, the entire essence atomizer is more compact and simple. Since the essence atomizer is integrally formed into a body, so it requires less components, and the production processes can be reduced. As such, it is able to achieve mass production, good quality, water tight seal, and long service life. In application, the essence atomizer can be put into an outer shell of various shapes, and then it is connected to an essence container to produce atomizing essence.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from the detailed descriptions.

BRIEF DESCRIPTION OF THE DRAWINGS

The related drawings in connection with the detailed descriptions of the present invention to be made later are described briefly as follows, in which.

DETAILED DESCRIPTION OF THE PREFERRED EMBODIMENT

The purpose, construction, features, functions and advantages of the present invention can be appreciated and understood more thoroughly through the following detailed descriptions with reference to the attached drawings.

Refer to FIGS. 1 to 7 respectively for an exploded view of an essence atomizer having an integrally formed universal connector according to the present invention; a top view of an essence atomizer having an integrally formed universal connector according to the present invention; a cross section view of an essence atomizer having an integrally formed universal connector according to the present invention; a perspective view of an essence atomizer having an integrally formed universal connector according to the first embodiment of the present invention; a cross section view of an essence atomizer having an integrally formed universal connector according to the first embodiment of the present invention; a perspective view of an essence atomizer having an integrally formed universal connector according to a second embodiment of the present invention; and a cross section view of an essence atomizer having an integrally formed universal connector according to a second embodiment of the present invention.

The present invention provides an essence atomizer having an integrally formed universal connector, comprising: an atomizer universal connector 1 integrally formed into a pipe piece, having a first end portion 11 and a second end portion 12 opposite to the first end portion 11, an inside bend portion 13 is disposed between the first end portion 11 and a second end portion 12, such that an angle is formed between a pipe port 120 of the second end portion 12 and a pipe port 110 of the first end portion 11, the pipe port 110 of the first end portion 11 is greater than the pipe port 120 of the second end portion 12, on the pipe port 110 of the first end portion 11 is disposed inward in sequence a front connection port 111, inner threads 112, and a bottom groove 113 for placing a rubber ring 114, on the pipe port 120 of the second end portion 12 is disposed an expansion ring 121 connected to an atomizer plate 122, an oil prevention pad 123, a nozzle cover 2.

Figure 1:
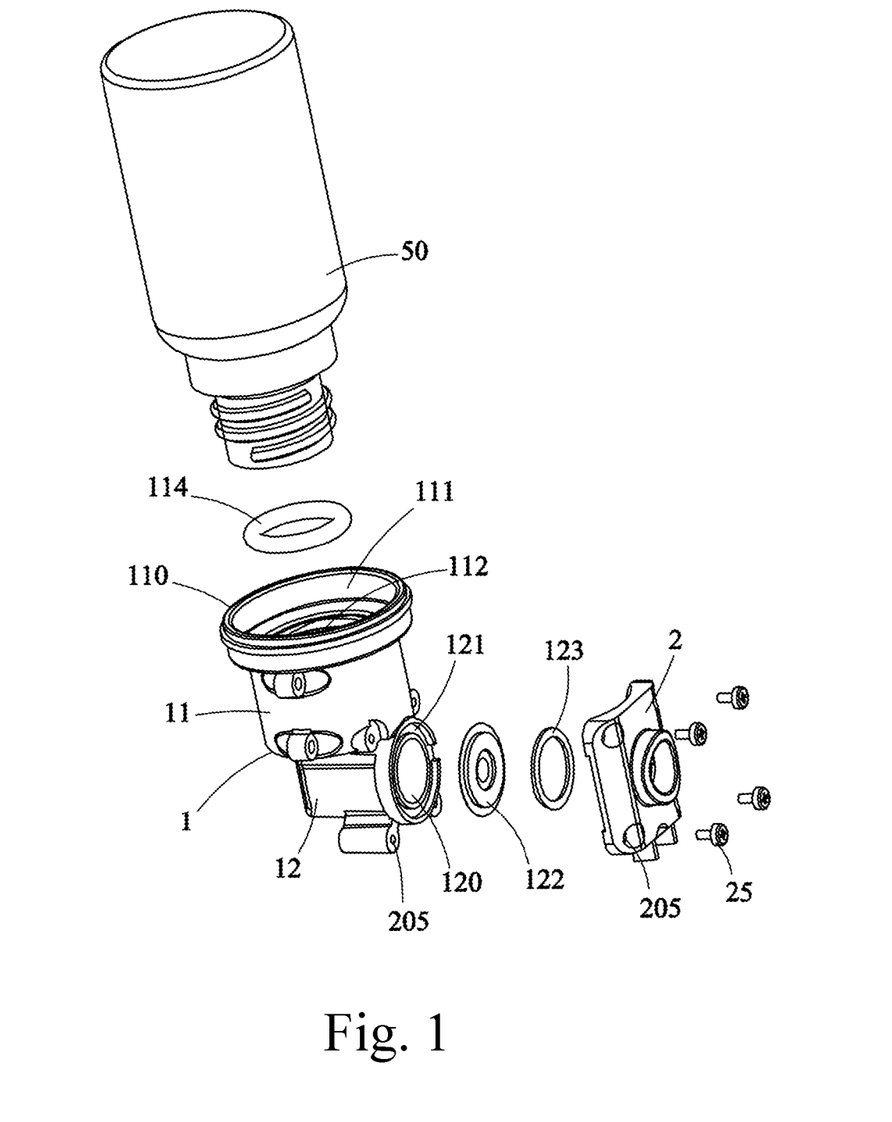
FIG. 1 is an exploded view of an essence atomizer having an integrally formed universal connector according to the present invention.
Figure 2:
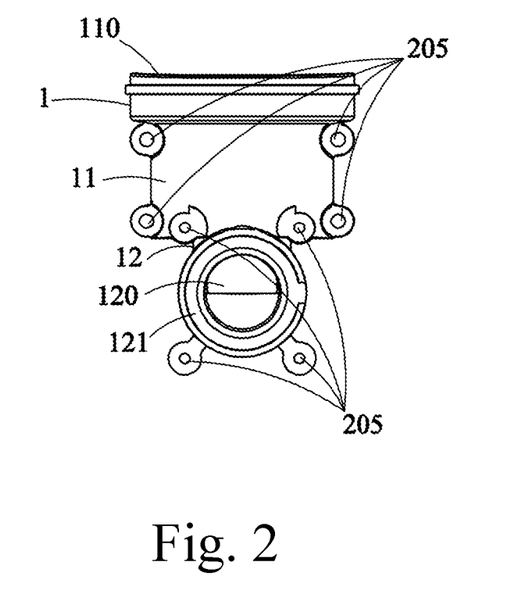
FIG. 2 is a top view of an essence atomizer having an integrally formed universal connector according to the present invention.
Figure 3:
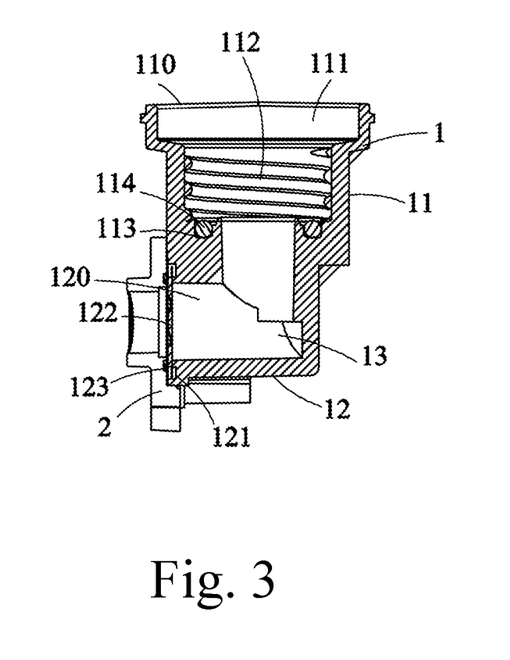
FIG. 3 is a cross section view of an essence atomizer having an integrally formed universal connector according to the present invention.

The nozzle cover 2 is formed into a protrusion plate having a hole. On the four corners of the nozzle cover 2 and around the perimeter of the expansion ring 121 are provided with a plurality of hole locking portions 205, to be fixed and locked by screws 25.

Figure 5:
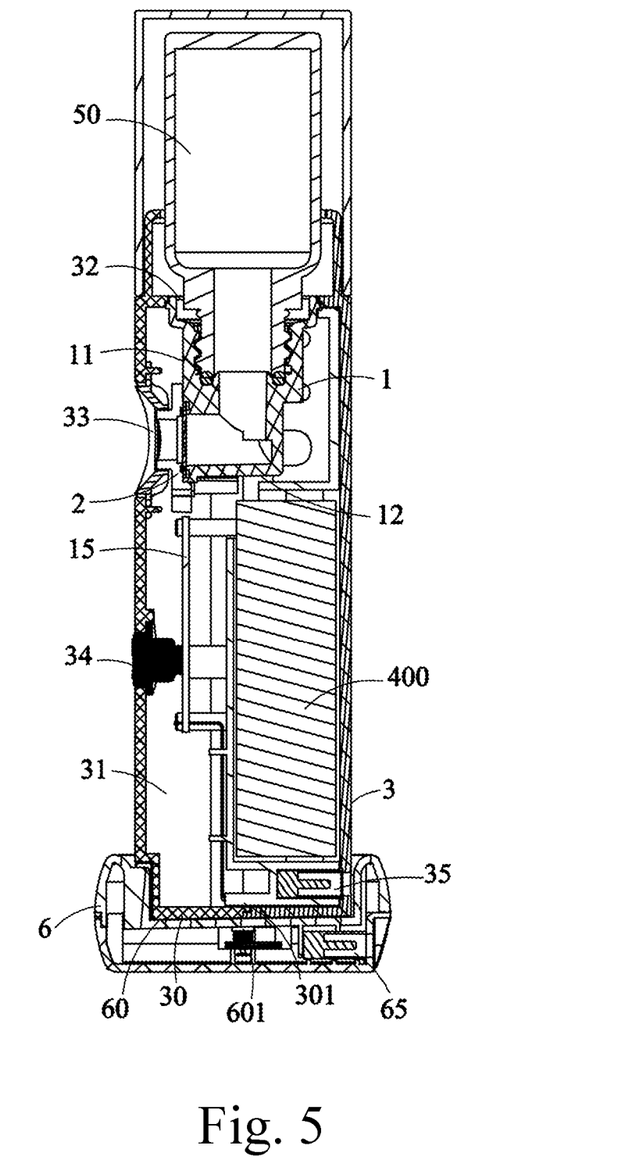
FIG. 5 is a cross section view of an essence atomizer having an integrally formed universal connector according to the first embodiment of the present invention.
Figure 7:
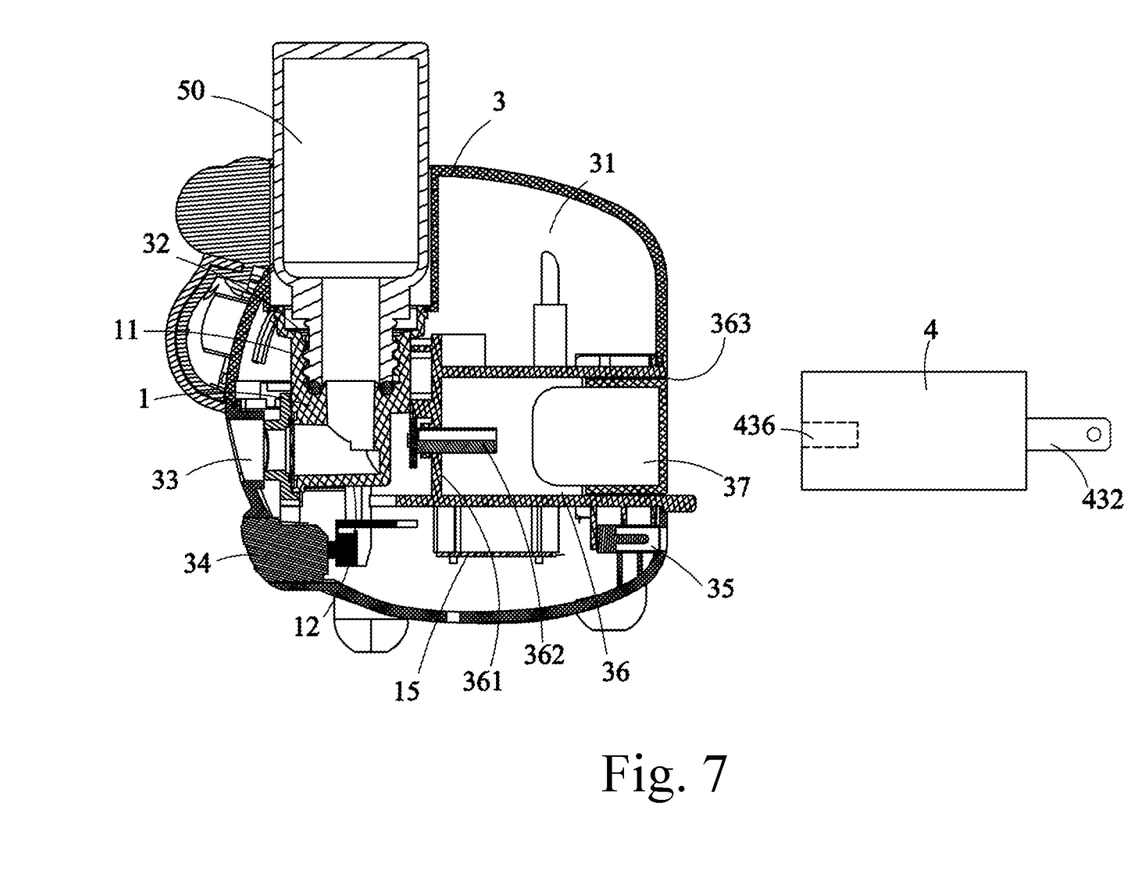
FIG. 7 is a cross section view of an essence atomizer having an integrally formed universal connector according to a second embodiment of the present invention.

The present invention has the advantages in that, the entire essence atomizer is more compact in structure and simple in operation. Since the essence atomizer is integrally formed into a piece, so it requires less components, and the production processes can be reduced. As such, it is able to achieve mass production, good quality, water tight seal, and long service life. As shown in FIGS. 5 and 7, in practice, the essence atomizer can be put into outer shells 3 of various shapes, and then connected to an essence container 50 to produce atomizing essence, to avoid the problem of the Prior Art of essence liquid leaking from the atomizer universal connector 1.

As shown in FIGS. 1 to 7, the first end portion 11 is of a cylindrical shape, while the second end portion 12 is of a tapering protrusion shape. The minimum distance between the first end portion 11 and the second end portion 12 is 30.4 cm. The minimum diameter of the pipe port 110 of the first end portion 11 is Φ28.5, while the minimum diameter of the expansion ring 121 at the second end portion 12 is Φ14. The diameter of the atomizer plate 122 is in a range of 13 mm to 14 mm. At the second end portion 12 of the atomizer universal connector 1, and on both sides of an expansion ring 121 are provided with at least four hole locking portions 205, for connecting and locking the nozzle cover 2. And on both sides of the first end portion 11 of the atomizer universal connector 1 are provided with at least four hole locking portions 205 spaced apart, for locking and connecting in an inner cavity 31 of an outer shell 3.

The outer shell 3 is a of one of the following shapes: a column, a cube, a sphere, an elliptical sphere, and a polygon.

Further, as shown in FIGS. 4 to 7, the outer shell 3 is used to wrap around and cover the atomizer universal connector 1. The outer shell 3 further includes: an electric circuit board 15 connected thereto; a placement port 32 disposed at the first end portion 11 of the atomizer universal connector 1 opposite to the outer shell 3; a sprout 33 disposed at the a nozzle cover 2 opposite to the second end portion 12 ; a control key 34 on the outer shell 3, connected to the electric circuit board 15, the electric circuit board 15 is used to control the atomizer plate 122 to work; a DC power jack 35 disposed on the outer shell 3, for connecting it to a DC power source, to supply power to the electric circuit board 15 (as shown in FIG. 5).

Figure 4:
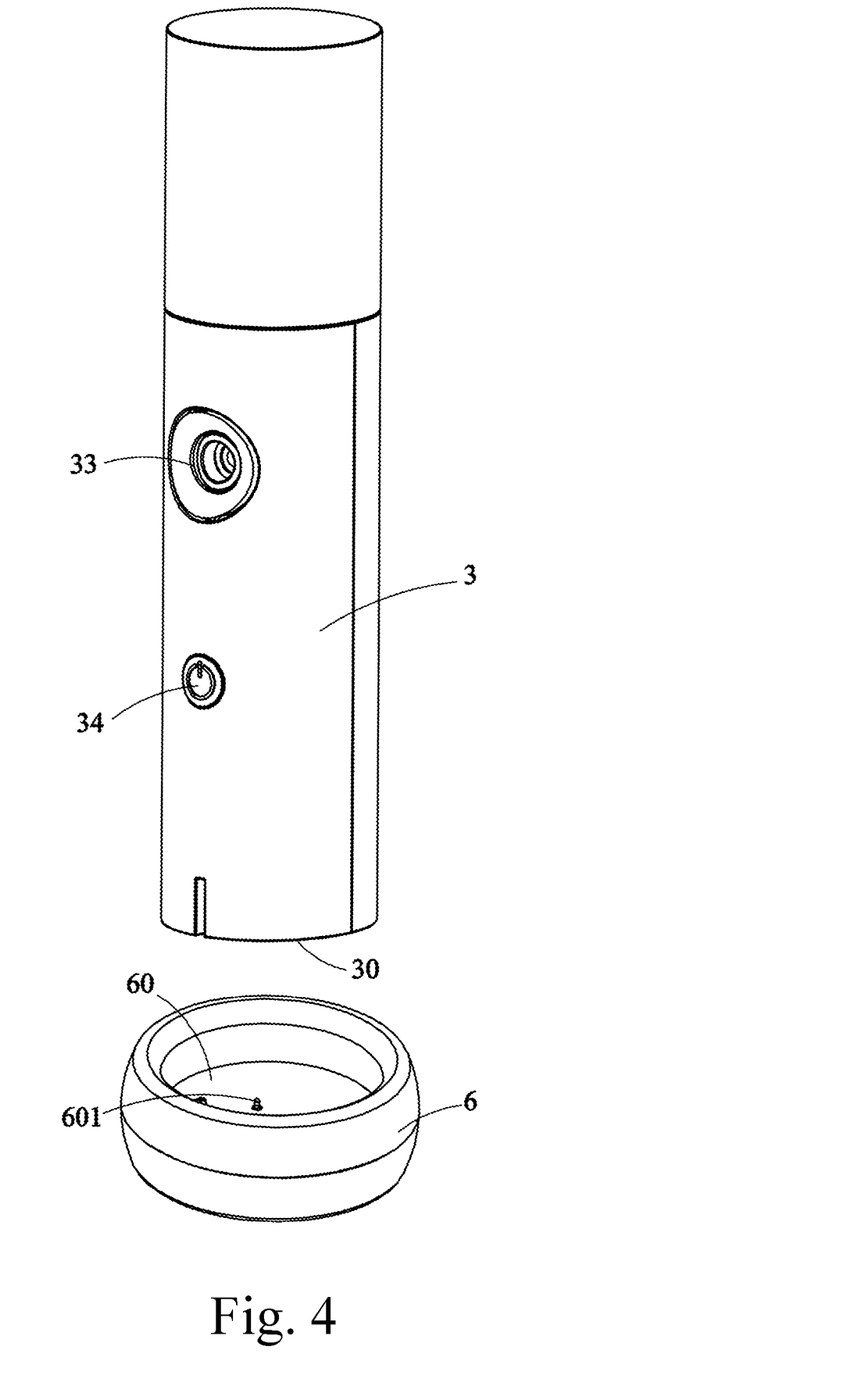
FIG. 4 is a perspective view of an essence atomizer having an integrally formed universal connector according to the first embodiment of the present invention.

As shown in FIGS. 4 and 5, in the first embodiment of the present invention, the outer shell 3 can be designed into a cylindrical shape having an upper cover, but the present invention is not limited to this. The rear portion of the outer shell 3 further includes: a placement portion 30, and at least two metal contact points 301 are disposed below, to be connected inside the outer shell 3 to a rechargeable battery 400, to supply power to the electrical circuit board 15; and a charging seat 6, on which is disposed a depressed place 60, for removably inserting it into the placement portion 30 of the outer shell 3, on the charging seat 6 is disposed a DC power jack 35 and a conduction plate 601 is embedded in the depressed place 60, to contact and supply power to the two metal contact points 301 in the placement portion 30 of the outer shell 3. In the present invention, a rechargeable battery 400 is provided, so that the essence atomizer can be carried to any place to perform essence atomizing.

Figure 6:
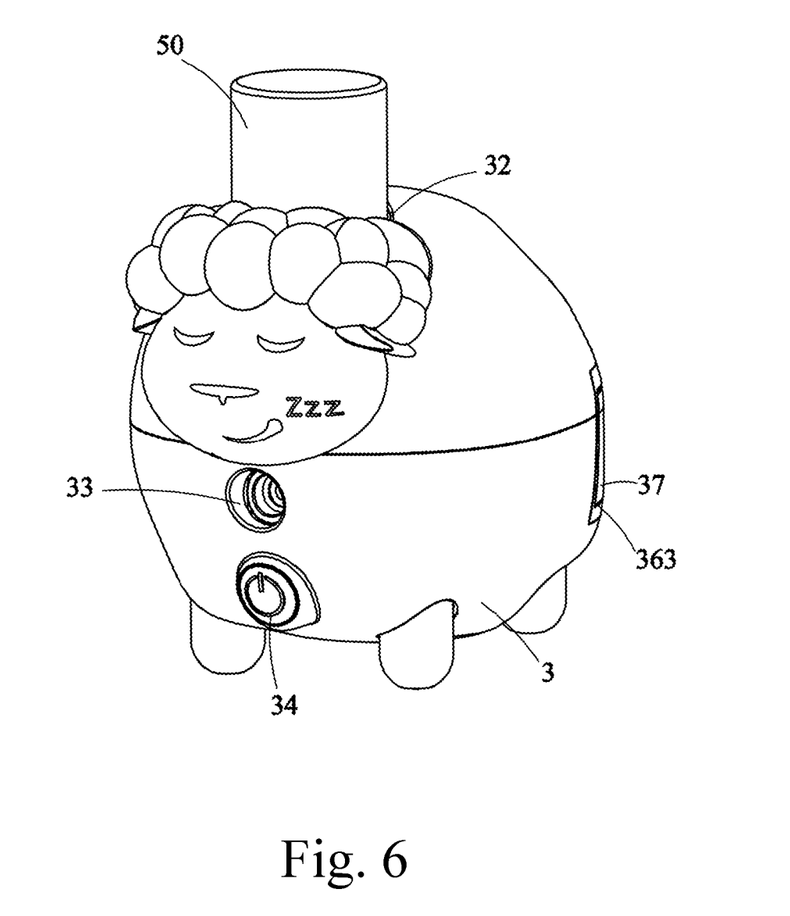
FIG. 6 is a perspective view of an essence atomizer having an integrally formed universal connector according to a second embodiment of the present invention.

As shown in FIGS. 6 and 7, in the second embodiment of the present invention, the outer shell 3 can be made into a shape of a sheep doll, but the present invention is not limited to this. Behind the outer shell 3 is further provided with a depression 36, an USB plug 362 is provided on a bottom portion 361 of the depression 36, a rear cover 37 is disposed at an opening 363 of the depression 36; and an assembled power connector 4, removably inserted in the depression 36, one end of the assembled power connector 4 is provided with a USB socket 436, to be inserted into the USB plug 362, and the other end of the assembled power connector 4 protrudes out a back side of the outer shell 3, and is provided with a power plug 432 for connecting it to a socket (not shown) of a utility power source. In the present invention, the essence atomizer can be put on a fixed place, such as on a table. Or, a power plug can be put on the back of the essence atomizer, to be inserted into a socket on a wall, to become a wall-insertion-type essence atomizer. Further, LEDs can be put into the essence atomizer, to make it a wall-insertion-type essence atomizer having function of night lights.

Figure 8:
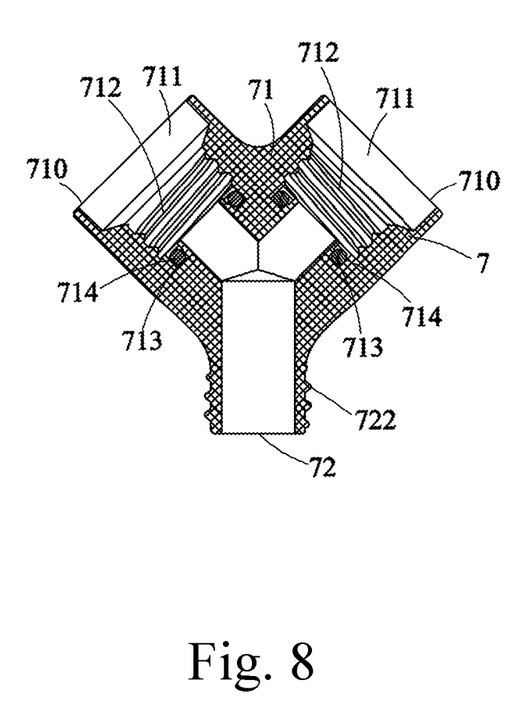
FIG. 8 is a cross section view of an expansion universal connector according to the present invention.
Figure 9:
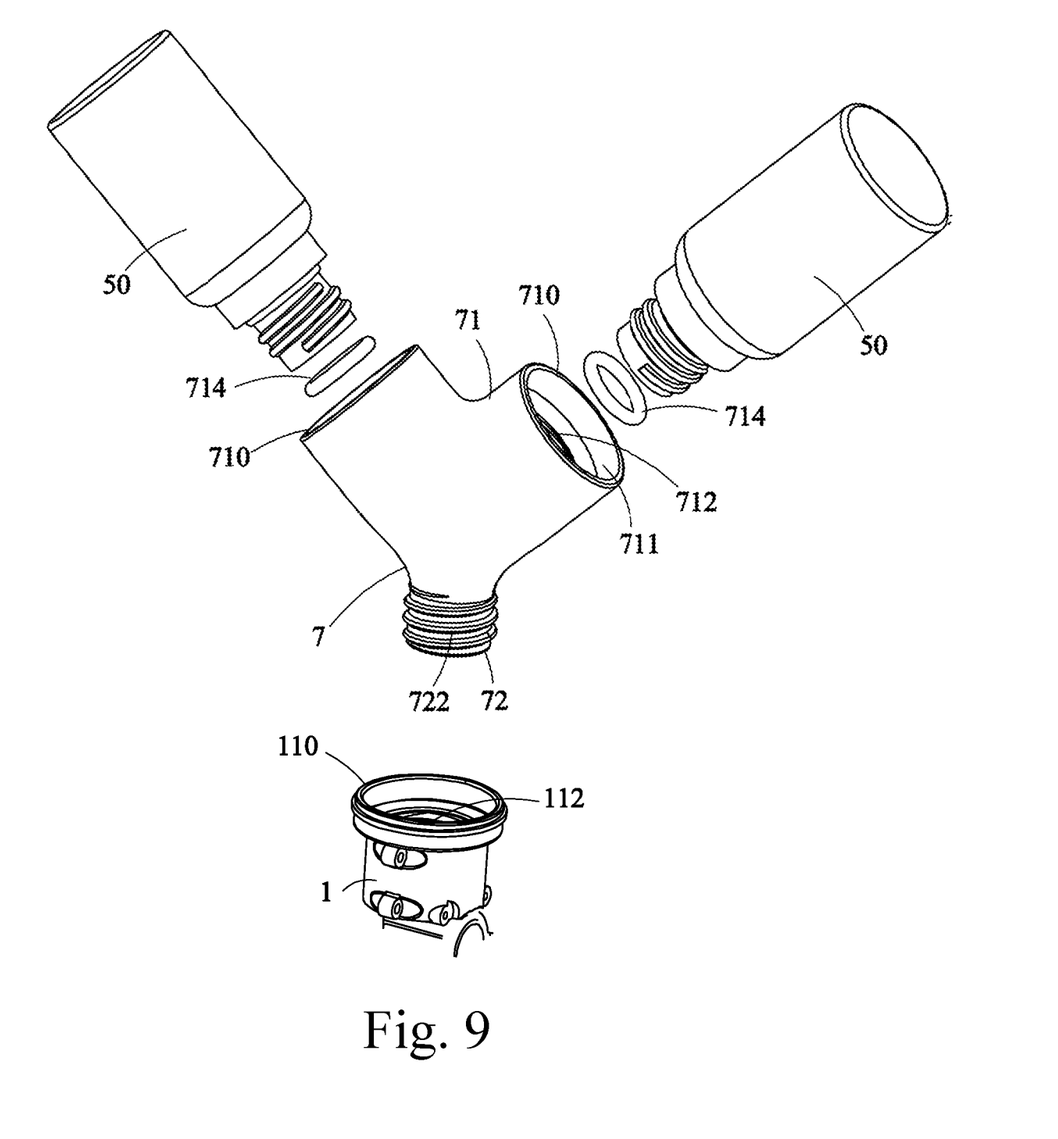
FIG. 9 is a perspective view of an expansion universal connector according to the present invention.

As shown in FIGS. 8 and 9, in the present invention, a mixture of atomized essences can be obtained through using the essence atomizer. Wherein, an expansion universal connector 7 is disposed on the pipe port 110 of the first end portion 11 for the atomizer universal connector 1, the expansion universal connector 7 is formed integrally into a pipe piece, and having a split expansion end 71 and a single pipe connector end 72 connected with each other. On the single pipe connector end 72 is disposed outer threads 722 for being locked into the inner threads 112 of the pipe port 110 of the first end portion 11. On the split expansion end 71 is provided with at least two pipe ports 710 having an angle formed between them. From each of the pipe ports 710 is disposed inward in sequence a front connection port 711, inner threads 712, and a bottom groove 713 for receiving a rubber ring 714, to form at least two universal connectors, to be connected and locked onto a corresponding number of an essence containers 50 respectively, thus obtaining a mixture of atomized essences as required.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. An essence atomizer having an integrally formed universal connector, comprising:
    an atomizer universal connector formed integrally into a pipe piece, having a first end portion and a second end portion opposite to the first end portion, the first end portion being of a cylindrical shape, an inside bend portion being disposed between the first end portion and the second end portion, a pipe port of the second end portion forming an angle with a pipe port of the first end portion, an inner diameter of the pipe port of the first end portion being greater than an inner diameter of the pipe port of the second end portion, on the pipe port of the first end portion being disposed inward in sequence a front connection port, inner threads, and a bottom groove for placing a rubber ring, to form a universal connector connected to an opposite essence container, on the pipe port of the second end portion being disposed an expansion ring connected to an atomizer plate, an oil prevention pad, a nozzle cover formed into a protrusion plate having a hole; and
    an outer shell, used to wrap around and cover the atomizer universal connector, the outer shell including an electric circuit board connected thereto; a placement port disposed at the first end portion of the atomizer universal connector a sprout disposed at the nozzle cover opposite to the second end portion; a DC power jack disposed on the outer shell, for connecting to a DC power source to supply power to the electric circuit board; and a control key on the outer shell connected to the electric circuit board, the electric circuit board being connected to and controlling an operation of the atomizer plate,
    wherein the outer shell further includes:
    a placement portion, and at least two metal contact points are disposed on a bottom thereof to be connected inside the outer shell to a rechargeable battery, to supply power to the electrical circuit board; and
    a charging seat, on which being disposed a depressed place, the placement portion of the outer shell being removably inserted into the charging seat, on the charging seat being disposed a DC power jack, and a conduction plate being embedded in the depressed place to contact and supply power to the two metal contact points in the placement portion of the outer shell,
    wherein four corners of the expansion ring are provided with four hole locking portions respectively, each of four corners of the nozzle cover is provided with a hole locking portion for being locked and connected by a screw, and outers surface of the first end portion of the atomizer universal connector is provided with at least four hole locking portions spaced apart for being locked and connected in an inner cavity of the outer shell.

2. The essence atomizer having an integrally formed universal connector as claimed in claim 1, wherein the outer shell is of one of the following shapes: a column, a cube, a sphere, an elliptical sphere, and a polygon.

* * * * *